(12) United States Patent
Caspers (10) Patent No.: US 11,116,649 B2
(45) Date of Patent: Sep. 14, 2021

(54) SOCKET LINER INTERFACE SYSTEM

(71) Applicant: NETTwork Manufacturing, Inc., Rice, MN (US)

(72) Inventor: Carl A. Caspers, Sartell, MN (US)

(73) Assignee: NETTwork Manufacturing, Inc., Rice, MN (US)

(*) Notice: Subject to any disclaimer, the term of this patent is extended or adjusted under 35 U.S.C. 154(b) by 165 days.

(21) Appl. No.: 16/051,845

(22) Filed: Aug. 1, 2018

(65) Prior Publication Data

US 2019/0038439 A1 Feb. 7, 2019

Related U.S. Application Data

(60) Provisional application No. 62/540,634, filed on Aug. 3, 2017.

(51) Int. Cl.
*A61F 2/78* (2006.01)
*A61F 2/80* (2006.01)
*A61F 2/60* (2006.01)

(52) U.S. Cl.
CPC ...... *A61F 2/7812* (2013.01); *A61F 2002/607* (2013.01); *A61F 2002/785* (2013.01); *A61F 2002/7818* (2013.01); *A61F 2002/802* (2013.01)

(58) Field of Classification Search
CPC .................................. A61F 2/7812–2002/785
See application file for complete search history.

(56) References Cited

U.S. PATENT DOCUMENTS

| | | | |
|---|---|---|---|
| 37,637 A | 2/1863 | Parmelee | |
| 4,923,474 A * | 5/1990 | Klasson | A61F 2/80 |
| | | | 623/33 |
| 5,081,210 A | 1/1992 | Sarpeshkar et al. | |
| 5,258,037 A | 11/1993 | Caspers | |
| 5,376,132 A | 12/1994 | Caspers | |
| 5,534,034 A | 7/1996 | Caspers | |
| 5,549,709 A | 8/1996 | Caspers | |
| 5,571,208 A | 11/1996 | Caspers | |
| 5,708,985 A * | 1/1998 | Ogden | D04B 1/04 |
| | | | 2/239 |
| 5,735,906 A | 4/1998 | Caspers | |

(Continued)

FOREIGN PATENT DOCUMENTS

EP 0346 697 A2 * 12/1989 .......... A61F 2/7812

*Primary Examiner* — David H Willse
(74) *Attorney, Agent, or Firm* — Pauly, DeVries Smith & Deffner LLC (57) ABSTRACT

Embodiments herein relate to socket liners for prosthetic systems and prosthetic systems including the same. In an embodiment, a socket liner for a prosthetic system is included having a polymeric wall member defining an interior volume. The polymeric wall member having an inner surface bordering the interior volume and an outer surface. The polymeric wall member can include an anterior side, a posterior side, a first lateral side and a second lateral side the second lateral side opposite the first lateral side. A plurality of horizontal ridges can be disposed on the inner surface of the polymeric wall member on the first lateral side and the second lateral side. A plurality of vertical channels can be disposed on the inner surface of the polymeric wall member on the anterior side and the posterior side. Other embodiments are also included herein.

19 Claims, 9 Drawing Sheets

(56) References Cited

U.S. PATENT DOCUMENTS

| | | | |
|---|---|---|---|
| 5,888,216 A * | 3/1999 | Haberman | A61F 2/7812 623/36 |
| 5,904,722 A | 5/1999 | Caspers | |
| D429,335 S | 8/2000 | Caspers et al. | |
| 6,136,039 A | 10/2000 | Kristinsson et al. | |
| 6,508,842 B1 | 1/2003 | Caspers | |
| 6,554,868 B1 | 4/2003 | Caspers | |
| 6,626,952 B2 | 9/2003 | Janusson et al. | |
| 6,645,253 B2 | 11/2003 | Caspers | |
| 6,726,726 B2 | 4/2004 | Caspers | |
| 6,761,742 B2 | 7/2004 | Caspers | |
| D503,802 S | 4/2005 | Bjarnason | |
| 6,926,742 B2 | 8/2005 | Caspers et al. | |
| 6,974,484 B2 | 12/2005 | Caspers | |
| 7,019,082 B2 | 3/2006 | Matyjaszewski et al. | |
| 7,025,793 B2 | 4/2006 | Egilsson | |
| 7,118,602 B2 | 10/2006 | Bjarnason | |
| 7,150,762 B2 | 12/2006 | Caspers | |
| 7,169,189 B2 | 1/2007 | Bjarnason et al. | |
| 7,235,108 B2 | 6/2007 | Carstens | |
| 7,377,944 B2 | 5/2008 | Janusson et al. | |
| 7,749,281 B2 | 7/2010 | Egilsson | |
| 7,909,884 B2 | 3/2011 | Egilsson et al. | |
| 7,922,775 B2 | 4/2011 | Caspers | |
| 8,052,760 B2 | 11/2011 | Egilsson et al. | |
| 8,097,043 B2 | 1/2012 | Egilsson | |
| 8,114,167 B2 | 2/2012 | Caspers | |
| 8,308,817 B2 | 11/2012 | Egilsson et al. | |
| 8,480,759 B2 * | 7/2013 | Pacanowsky | A61F 2/70 623/36 |
| 8,597,368 B2 | 12/2013 | Bjarnason et al. | |
| 8,758,449 B2 | 6/2014 | Caspers | |
| 8,828,094 B2 | 9/2014 | Halldorsson | |
| 8,894,719 B2 | 11/2014 | Egilsson et al. | |
| 8,940,057 B2 | 1/2015 | Asgeirsson | |
| 8,956,422 B2 | 2/2015 | Halldorsson | |
| 9,066,821 B2 | 6/2015 | Egilsson et al. | |
| 9,248,032 B2 | 2/2016 | Gunnarsson et al. | |
| 9,498,355 B2 | 11/2016 | Halldorsson | |
| 9,556,305 B2 | 1/2017 | Kung | |
| 9,566,175 B2 | 2/2017 | Halldorsson | |
| 9,629,732 B2 | 4/2017 | Egilsson et al. | |
| 9,788,977 B2 | 10/2017 | Halldorsson et al. | |
| 2001/0005798 A1 | 6/2001 | Caspers | |
| 2001/0016781 A1 | 8/2001 | Caspers | |
| 2002/0087215 A1 | 7/2002 | Caspers | |
| 2002/0091449 A1 | 7/2002 | Caspers et al. | |
| 2003/0191539 A1 | 10/2003 | Caspers | |
| 2004/0024322 A1 | 2/2004 | Caspers | |
| 2004/0030411 A1 | 2/2004 | Caspers | |
| 2004/0098136 A1 | 5/2004 | Caspers | |
| 2004/0143345 A1 | 7/2004 | Caspers | |
| 2004/0163278 A1 | 8/2004 | Caspers et al. | |
| 2004/0167638 A1 | 8/2004 | Caspers | |
| 2004/0181290 A1 | 9/2004 | Caspers | |
| 2005/0131549 A1 | 6/2005 | Caspers | |
| 2005/0267599 A1 * | 12/2005 | Bjarnason | A61F 2/7812 623/36 |
| 2009/0036999 A1 * | 2/2009 | Egilsson | A61F 2/7812 623/36 |
| 2010/0312359 A1 | 12/2010 | Caspers | |
| 2010/0312360 A1 | 12/2010 | Caspers | |
| 2011/0202143 A1 | 8/2011 | Caspers | |
| 2012/0173000 A1 | 7/2012 | Caspers | |
| 2012/0173001 A1 | 7/2012 | Caspers | |
| 2013/0190895 A1 | 7/2013 | Kristinsdottir | |
| 2013/0331952 A1 | 12/2013 | Halldorsson et al. | |
| 2014/0200682 A1 | 7/2014 | Egilsson et al. | |
| 2015/0079014 A1 | 3/2015 | Ingvarsson et al. | |
| 2017/0056212 A1 * | 3/2017 | Jonsson | A61F 7/00 |
| 2017/0151073 A1 | 6/2017 | Halldorsson | |
| 2017/0216057 A1 | 8/2017 | Egilsson et al. | |

* cited by examiner

SOCKET LINER INTERFACE SYSTEM

This application claims the benefit of U.S. Provisional Application No. 62/540,634, filed Aug. 3, 2017, the content of which is herein incorporated by reference in its entirety.

FIELD

Aspects herein relate to socket liners for prosthetic systems and prosthetic systems including the same.

BACKGROUND

A prosthesis is a device that replaces all or a portion of a limb that has been lost by an amputee. As such, a prosthesis can also be referred to as an artificial limb. A prosthesis can help an individual in performing various activities such as exercising, sports, walking, recreation, carrying things, etc. The goal with a prosthesis is to allow the patient to function as well as, or nearly as well as, they would if they were not missing a limb with as little discomfort as possible.

One type of prosthesis is known as a below-knee prosthesis. A below-knee (or transtibial) prosthesis is for below knee amputees. A below-knee amputation (BKA) is an amputation often performed for foot and ankle problems which could be caused by a traumatic injury or a disease state. The goal of the amputation is to remove unhealthy tissue and create a remaining leg that is less painful and more useful.

SUMMARY

Aspects here relate to socket liners for prosthetic systems and prosthetic systems including the same. In an embodiment, a socket liner for a prosthetic system is included having a polymeric wall member defining an interior volume. The polymeric wall member having an inner surface bordering the interior volume and an outer surface on the opposite side of the polymeric wall member from the inner surface. The polymeric wall member can include an anterior side, a posterior side, a first lateral side and a second lateral side the second lateral side opposite the first lateral side. The polymeric wall member can include an open upper end and a closed lower end. A plurality of horizontal ridges can be disposed on the inner surface of the polymeric wall member on the first lateral side and the second lateral side. A plurality of vertical channels can be disposed on the inner surface of the polymeric wall member on the anterior side and the posterior side.

In an embodiment, a socket liner interface system is included. The system can include a prosthesis comprising a socket configured to receive a residual limb and a socket liner comprising a polymeric wall member defining an interior volume the polymeric wall member having an inner surface bordering the interior volume and an outer surface on the opposite side of the polymeric wall member from the inner surface. The polymeric wall member can include an anterior side, a posterior side, a first lateral side, and a second lateral side the second lateral side opposite the first lateral side. The polymeric wall member comprising an open upper end and a closed lower end. A plurality of horizontal ridges can be disposed on the inner surface of the polymeric wall member on the first lateral side and the second lateral side. A plurality of vertical channels can be disposed on the inner surface of the polymeric wall member on the anterior side and the posterior side.

In an embodiment, a method of making a socket liner for a prosthesis is included. The method can include taking a cast of a residual limb and forming a polymeric wall member according to dimensions of the cast, the polymeric wall member defining an interior volume the polymeric wall member having an inner surface bordering the interior volume and an outer surface on the opposite side of the polymeric wall member from the inner surface. The polymeric wall member can include an anterior side, a posterior side, a first lateral side, and a second lateral side, the second lateral side opposite the first lateral side. The polymeric wall member comprising an open upper end and a closed lower end. A plurality of horizontal ridges can be disposed on the inner surface of the polymeric wall member on the first lateral side and the second lateral side and a plurality of vertical channels can be disposed on the inner surface of the polymeric wall member on the anterior side and the posterior side.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects can be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Advances in prosthetic socket design provide the skilled, knowledgeable and committed prosthetist with the tools necessary to substantially improve the quality of life of their patients. However, the transtibial socket interface will always be an imperfect substitute for the bone-to-bone connection lost during amputation. The major deficiencies of the transtibial socket interface are deformation of the soft tissues and slipping between the layers. These deficiencies are responsible for the amputee having soft tissue breakdown and/or pain, and poor spatial awareness and control of the prosthetic leg. In addition, further deficiencies that need to be resolved are sweat removal and odor prevention between the gel liner and skin, and avoiding bunching of materials behind the knee.

Some prostheses use a socket liner (such as a polymeric socket liner) that covers a user's residual limb and interfaces with a socket that is shaped to receive the residual limb. Previous socket liner designs were created in accord with the belief that friction between the inside of the socket liner and the skin of the residual limb is bad. In particular, friction at this interface has been believed to play a role in the development of sores and irritation. This was partly because of the belief that movement of the skin of the residual limb relative to the inner surface of the socket liner was inevitable. Under that view, a low friction interface (such as provided by a smooth surface) was believed to result in less irritation and sores.

However, in accordance with embodiments herein, prosthetics and socket liners for prosthetics are provided that result in a high friction interface between the inside of the socket liner and the skin of the residual limb.

It has been discovered that the higher the friction, the lower the pressure needed to support a certain load and the less slippage that will occur. The reduction of slippage will reduce bone movement (e.g., movement of the bone relative to the socket). Reduced bone movement results in a stiffer interface with low frictional energy loss, which has the advantage of producing stability and comfort in the prosthesis.

In particular, the larger the surface area of the interface between the inside of the socket liner and the skin of the residual limb, the greater the coefficient of friction and therefore the greater the holding ability. As the coefficient of friction increases, maximum shear stress at a given pressure also increases, thus required pressure and slippage both are remarkably reduced.

High pressure is bad for multiple reasons. The higher the pressure that is required to stabilize the limb in the socket, the greater fluid loss that takes place. Higher pressure also results in the increased atrophy of underlying tissue over time. Thus, the high friction prosthetics and socket liners herein can allow for greater stabilization, reduced slippage, stiffer interface, reduced fluid loss, lower required pressures, greater comfort and reduced atrophy over time.

In addition, previous socket liner designs have encountered the problem of bunching behind the user's knee. This causes irritation, making the socket liner uncomfortable. However, embodiments of socket liners herein, include features to reduce the occurrence of bunching behind the user's knee.

Further, previous socket liner designs also fail to control moisture buildup caused by sweat, particularly where the socket liner is not tight against the skin, which can also cause the socket liner to rub against the user's skin, causing sores and irritation. Embodiments of socket liners herein, include features to control moisture buildup.

In accordance with various embodiments herein, the coefficient of friction for the interface between the inside of the socket liner and the skin of the residual limb can be substantially greater than an otherwise similar socket liner lacking various of the features included with embodiments herein. In accordance with various embodiments herein, the surface area of the interface between the inside of the socket liner and the skin of the residual limb can be substantially greater than an otherwise similar socket liner lacking various of the features included with embodiments herein, including but not limited to a plurality of horizontal ridges disposed on the inner surface of the polymeric wall member forming the socket liner on the first lateral side and the second lateral side, and a plurality of vertical channels disposed on the inner surface of the polymeric wall member on the anterior side and the posterior side.

Figure 1:
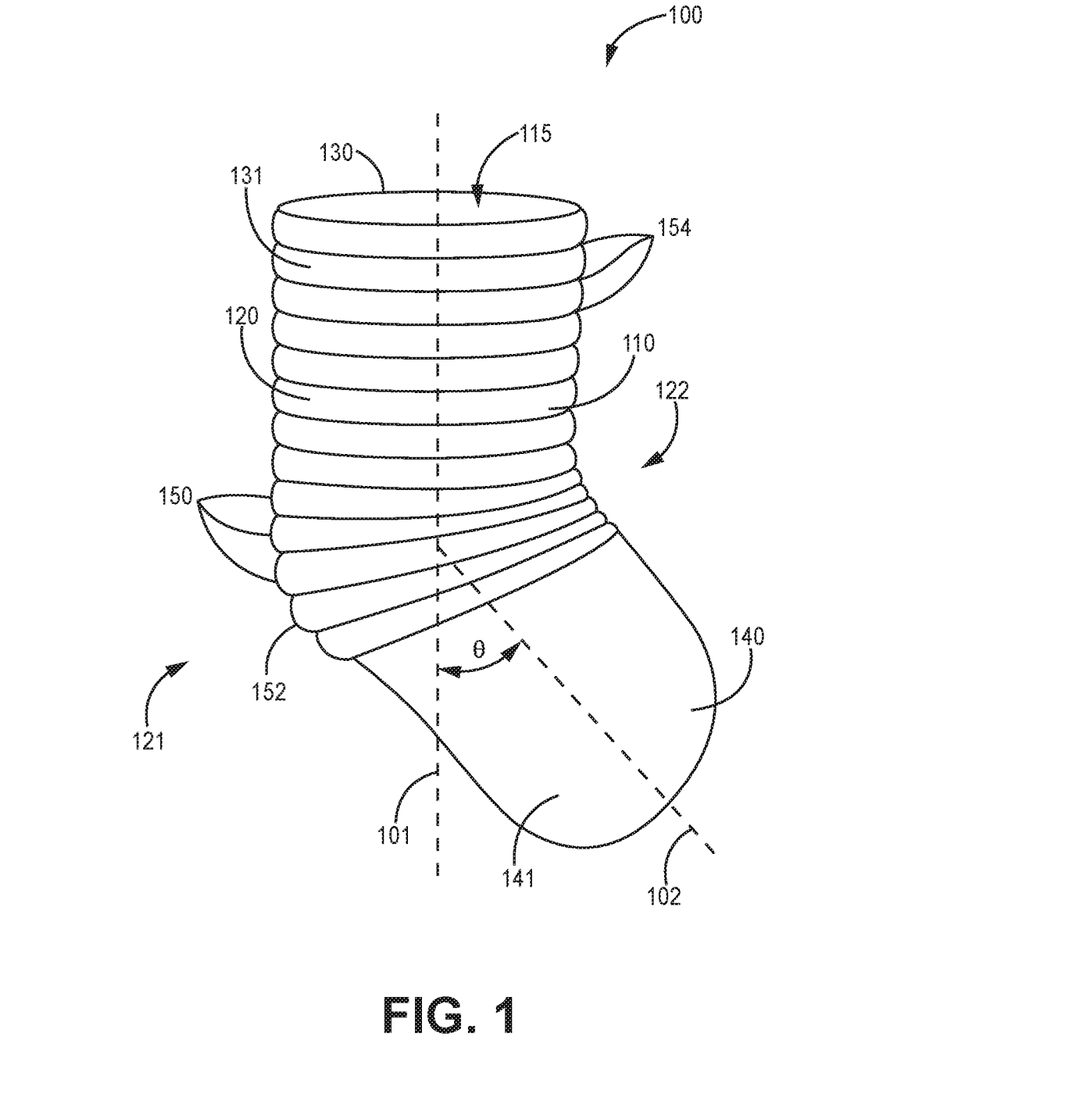
FIG. 1 is a side view of a socket liner for a prosthetic in accordance with various embodiments herein.

Referring now to FIG. 1, a side view is shown of a socket liner 100 for a prosthetic in accordance with various embodiments herein. The socket liner 100 includes a polymeric wall member 110 defining an interior volume 115. The socket liner 100 is shaped to cover a residual limb for an amputee. In some examples, the socket liner 100 is formed using a custom mold of the residual limb. In the example of FIG. 1, the socket liner 100 can be used with a transtibial (below knee) prosthesis. However, it will be appreciated that aspects of embodiments herein can also be used with socket liners for other types of prostheses. In some embodiments, the polymeric wall member 110 can be a unitary molded structure. In some examples, the polymeric wall member 110 is formed in a mold having both a female mold to create the outer surface 120 and a male mold to create the inner surface 220.

The socket liner 100, as defined by the polymeric wall member 110, has an open upper end 130 at an upper portion 131 of the polymeric wall member 110, and a closed lower end 140 at a lower portion 141 of the polymeric wall member 110. The size and shape of the upper portion 131 and the lower portion 141 of the socket liner 100 can be appropriate for the size and shape of the user's limb. In some examples, the closed lower end 140 has a substantially hemispherical shape. In some examples, the interior volume 115 conforms to the shape of a user's residual limb. In some examples, the interior volume 115 is sized to be slightly smaller than the residual limb. This will be discussed further below in relation to FIG. 7.

In the example of FIG. 1, the socket liner 100 has an anterior side 121 that aligns with an anterior portion of a knee joint. Opposite the anterior side 121 is a posterior side 122 of the socket liner 100. The posterior side 122 aligns with a posterior portion of the knee joint. In some examples, the socket liner 100 is pre-flexed, that is, shaped to conform to the geometry of a limb in partial flexion, with the knee slightly bent instead of having the knee fully extended. In such a case, the socket liner 100 includes a first lengthwise axis 101 that generally aligns with the user's femur, and a second lengthwise axis 102 that generally aligns with the user's lower leg. The first lengthwise axis 101 and the second lengthwise axis 102 are configured to intersect at or about the user's knee joint. In some examples, the angle between the first lengthwise axis 101 and the second lengthwise axis 102 is between 0 degrees and 45 degrees or between 10 degrees and 45 degrees. However, in some embodiments the socket liner 100 is not pre-flexed.

An outer surface 120 of the polymeric wall member 110 can have a plurality of exterior horizontal ridges 150. The exterior horizontal ridges 150 are provided to alleviate the problem of the polymeric wall member 110 bunching on the posterior side 122 of the socket liner 100. The exterior horizontal ridges 150 include a plurality of horizontal peaks 152 that are separated by a plurality of horizontal troughs 154 disposed on the outer surface 120 of the polymeric wall member 110. In some examples, the exterior horizontal ridges 150 extend 360 degrees around the outer circumference of the socket liner 100. In some examples, the exterior horizontal ridges 150 can extend for less than 360 degrees around the outer circumference. In some examples, the exterior horizontal ridges 150 extend up to the open upper end 130. In some examples, the exterior horizontal ridges 150 do not extend all the way down to the closed lower end 140.

In the example of FIG. 1, the exterior horizontal ridges 150 begin at the top of open upper end 130 and end just below the knee joint. In some embodiments the exterior horizontal ridges 150 begin below the top of open upper end 130 and end just below the knee joint. In some examples, when a user is wearing the socket liner, the exterior horizontal ridges 150 on the anterior side 121 of the socket liner 100 begin at the upper end 130 and end approximately 1, 2, 3, 4, 5, 6, 7, 8, 9, 10, 11, or 12 centimeters below the user's patella, or end at a distance falling within a range of distances between any of the foregoing. In some examples, the exterior horizontal ridges 150 on the posterior side 122 of the socket liner 100 begin at the upper end 130 and end approximately 1, 2, 3, 4, 5, 6, 7, 8, 9, 10, 11, or 12 centimeters below the bend of the user's knee. These measurements can, however, in some embodiments be individually determined by the dimensions of the user's body.

The exterior horizontal ridges 150 can have a uniform size and shape. However, in some examples, the size and shape of the exterior horizontal ridges 150 can be variable. In some examples, the troughs 154 can have equal widths around the entire circumference of the socket liner 100. In alternative examples, the troughs 154 can have variable widths. For example, a particular trough 154 can have a first width at the anterior side 121 of the socket liner 100, and a second width at the posterior side 122, where the trough width is smaller at the posterior side 122 then the anterior side 121. The exterior horizontal ridges 150 will be further discussed in relation to FIG. 5.

Figure 2:
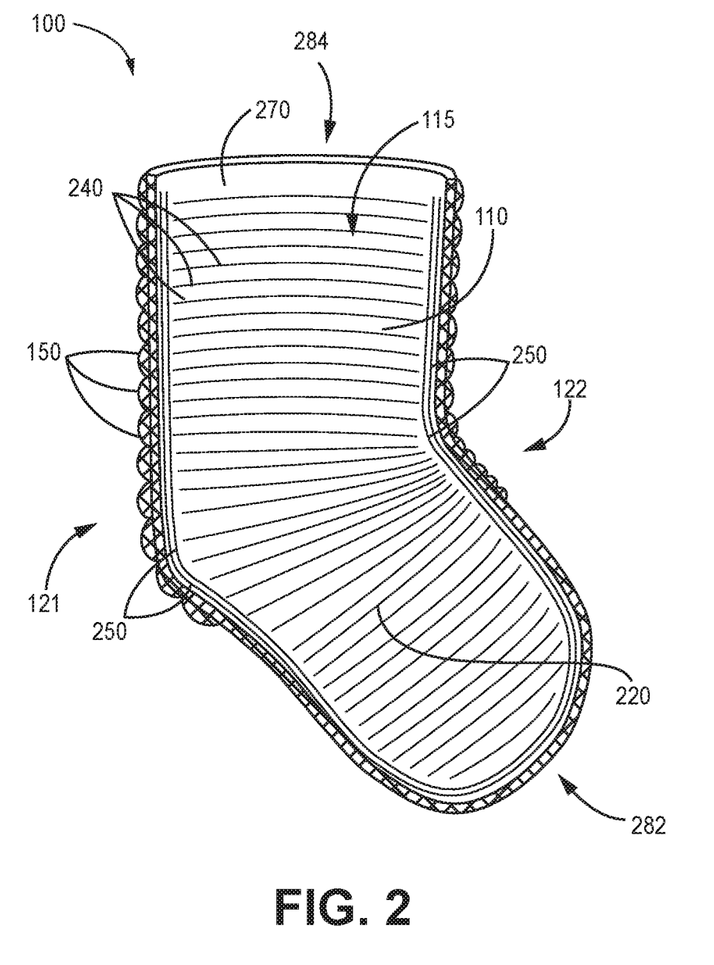
FIG. 2 is a cutaway view of the socket liner of FIG. 1.

Turning to FIG. 2, the socket liner 100 is shown in a cutaway view. In particular, the polymeric wall member 110 is shown as being cut along the midline of the anterior side 121 and the posterior side 122 to expose the interior volume 115 of the socket liner 100. The opposite lateral side of the polymeric wall member 110 is not shown in FIG. 2, but will generally be similar in shape and size. In some examples, the first lateral side and the second lateral side can be approximately mirror images of one another. However, because the socket liner 100 can be custom fit to each individual's body, the first lateral side and second lateral side of socket liner 100 can be asymmetrical in some embodiments.

The polymeric wall member 110 has an inner surface 220 bordering the interior volume 115. The inner surface 220 is on the opposite side of the polymeric wall member 110 from the outer surface 120. The inner surface 220 can be contoured to increase the surface area of the polymeric wall member 110 as compared to a wall member without contours. In some embodiments, the surface area of the inner surface 220 can be increased by at least 10, 20, 40, 60, 80, 100, 120, 140, 160, 180, 200, 250, 300, or even 400 percent compared with an otherwise identical inner surface lacking surface contours (such as horizontal ridges and/or vertical channels) described herein. In some embodiments, the increase in surface area can fall within a range between any of the foregoing percentages provided that the upper bound is greater than the lower bound.

In various embodiments, the contours can include peaks and troughs that contact the skin. In some examples, the peaks and troughs form parallel ridges or channels on the inner surface 220. However, other three-dimensional contour shapes are also contemplated herein to increase the surface area including, but not limited to, nubs, cones, raised dots, projections, hemispherical projections, and the like.

A first lateral side 270 of the polymeric wall member 110 has a plurality of horizontal ridges 240 disposed on the inner surface 220 of the polymeric wall member 110. As will be discussed later in relation to FIG. 5, the horizontal ridges 240 are composed of peaks and troughs. In some examples, the horizontal ridges 240 form parallel lines across the inner surface 220 of the first lateral side 270. The horizontal ridges 240 increase the surface area of the inner surface 220 as compared to a surface without horizontal ridges. This increased surface area increases the coefficient of friction between the polymeric wall member 110 and a user's skin. A higher coefficient of friction makes it more difficult for the polymeric wall member 110 to move with respect to the user's skin and therefore prevent it from rubbing against the user's skin. This can prevent sores and skin damage.

The inner surface 220 can also have a plurality of vertical channels 250 on the anterior side 121 and the posterior side 122 of the polymeric wall member 110. The vertical channels 250 can increase the surface area of the inner surface 220 on the anterior side 121 and the posterior side 122 as compared to a surface without vertical channels. As will be discussed further in relation to FIG. 4, in some embodiments the vertical channels 250 have peaks and troughs that can help to distribute moisture, such as sweat. In some examples, the peaks and the troughs of the vertical channels 250 form vertical parallel lines running from the open upper end 130 to the closed lower end 140.

As shown in FIG. 2, in various embodiments, exterior horizontal ridges 150 can be additive to the overall thickness of the socket liner in the area where they are present. For example, the exterior horizontal ridges 150 can effectively add to the maximum thickness of the polymeric wall member 110 in the area where they are present. Thus, in some embodiments, the difference between the thickness of the wall member 110 in the area of a peak versus the thickness of the wall member 110 in an adjacent area lacking a peak can be the height of the peak.

In some embodiments, the thickness of the polymeric wall member 110 can vary depending on the position along the overall length or width of the socket liner 100. For example, in some embodiments, the distal most portion 282 of the wall member 110 can be the thickest and the thickness can then taper towards the knee area (or middle area between the distal most portion 282 and the proximal most portion 284). In some embodiments, the proximal most portion 284 of the wall member 110 can be the thinnest. In some embodiments, the ratio of the maximum thickness of the wall member 110 at the distal most portion 282 to the maximum thickness of the wall member at the proximal most portion 284 can be about 1:1, 1.2:1, 1.4:1, 1.6:1, 1.8:1, 2:1, 2.5:1, 3:1, 4:1, or 5:1, or can fall within a range between any of the foregoing.

In some embodiments, surface features such as horizontal ridges and vertical channels can be substantially straight and even along their length. However, many different variations are also contemplated herein. For example, the width of ridges and/or channels can vary along their length.

Figure 3:
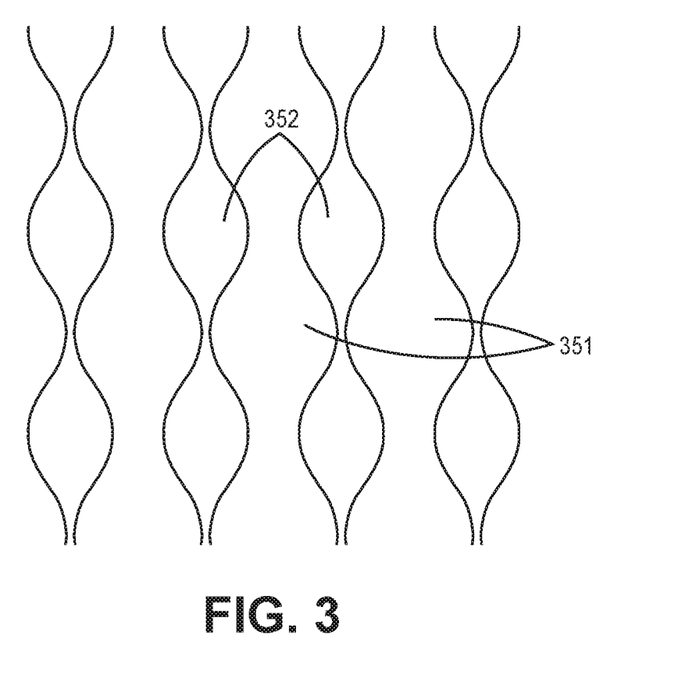
FIG. 3 is a close-up view of an inner surface for a socket liner in accordance with various embodiments herein.

FIG. 3 is a close-up view of an alternative inner surface for a socket liner for a prosthetic. In the example of FIG. 3, the inner surface 220 has a plurality of peaks 351 and a plurality of troughs 352 that form a lengthwise complementary sinusoidal pattern, instead of the straight vertical parallel lines shown in FIG. 2. The complementary sinusoidal pattern of the peaks 351 and troughs 352 along the length of the inner surface 220 can increase the coefficient of friction between the polymeric wall member 110 and the user's skin. The inner surface configuration of FIG. 3 could be used for either the horizontal ridges 240 or the vertical channels 250 or both. Other geometries of the peaks and troughs of the horizontal ridges 240 and the vertical channels 250 are also contemplated herein.

Figure 4:
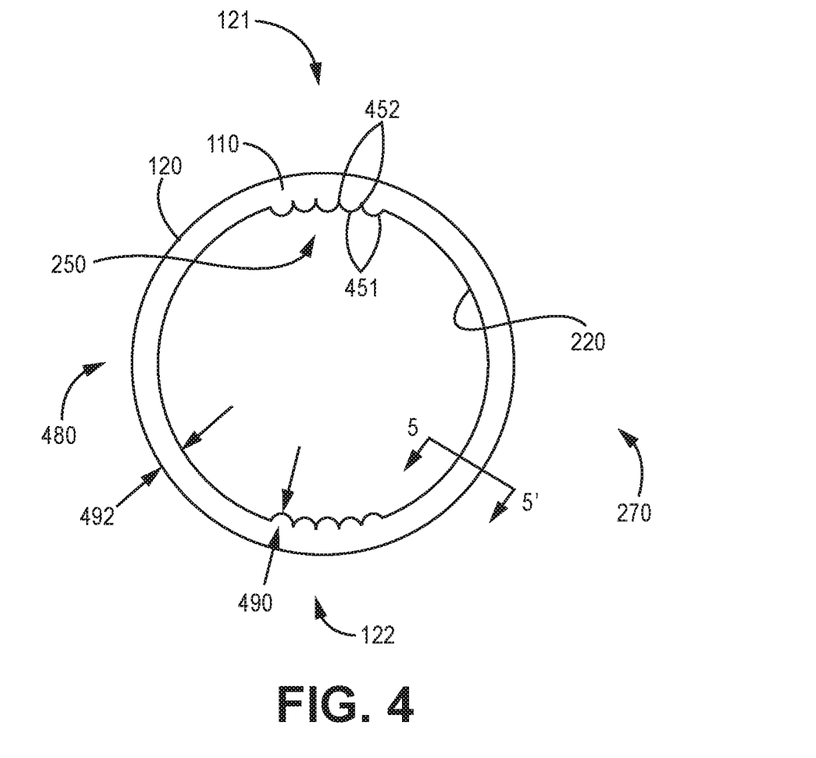
FIG. 4 is a cutaway top view of the socket liner of FIG. 1

FIG. 4 is a cutaway top view of the socket liner of FIG. 1. The polymeric wall member 110 includes an anterior side 121, a posterior side 122 opposite the anterior side 121, a first lateral side 270, and a second lateral side 480 opposite the first lateral side 270. The polymeric wall member 110 has a wall width 492. The wall width 492 can be constant or variable around the circumference of the polymeric wall member 110. In some embodiments, the wall width 492 can be about 1, 2, 3, 4, 5, 6, 7, 8, 9 or 10 millimeters, or can fall within a range between any of the foregoing.

The anterior side 121 and the posterior side 122 each have a plurality of vertical channels 250. The channels 250 include a plurality of peaks 451, and a plurality of troughs 452 disposed between the peaks 451.

In some examples, the peak-to-trough height 490 is between 0.05 mm and 2 mm. In some examples, the peak-to-trough height 490 is about 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0 mm, or in a range between any of the foregoing heights so long as the upper bound is greater than the lower bound. During use, if moisture appears between the inner surface 220 and the user's skin, the moisture can wick into the troughs 452 while the peaks 451 remain firmly contacted to the user's skin. Thus, the vertical channels 250 can serve as a transport conduit for moisture to move out of the socket liner 100.

In some examples, the cross-section of the peaks 451 and troughs 452 forms a sinusoidal pattern, with curved peaks 451 and curved troughs 452 of approximately the same shape and size. In alternative examples, the cross-section of the peaks 451 can be hemispherical and the cross-section of the troughs 452 can be planar or V-shaped. Other cross-sectional shapes are also contemplated herein.

In some examples, the vertical channels 250 on the anterior side 121 and the posterior side 122 of the inner surface 220 cumulatively span approximately one third of the inside circumference of the polymeric wall member 110. In some examples, the vertical channels 250 span about 5, 10, 15, 20, 25, 30, 35, 40, 45, 50, 55, 60, 65, 70, 75, 80, 85 or 90 percent of the inside circumference of the polymeric wall member 110, or in a range between any of the foregoing provided that the upper bound is greater than the lower bound. In some embodiments, the vertical channels 250 span between 25 percent and 50 percent of the inside circumference of the polymeric wall member 110. In some examples, the vertical channels 250 at the anterior side 121 of the inner surface 220 span the same amount of circumference as the vertical channels 250 at the posterior side 122 of the inner surface 220. Other configurations are contemplated herein.

Likewise, in some examples, the horizontal ridges 240 on the inner surface 220 of the polymeric wall member 110 cumulatively span at least about 40, 50, 60, 70, 80, 90, 95 or 100 percent of the inside circumference of the polymeric wall member 110. In some embodiments, the horizontal ridges 240 on the inner surface 220 of the polymeric wall member 110 span a percentage of the inside circumference of the polymeric wall member 110 that falls within a range wherein any of the preceding can serve as the upper or lower bound of the range, provided that the upper bound is greater than the lower bound. In some embodiments, the horizontal ridges 240 on the inner surface 220 of the polymeric wall member 110 cumulatively span approximately two thirds of the inside circumference of the polymeric wall member 110. In alternative examples, the horizontal ridges 240 cumulatively span between 50 percent and 75 percent of the inside circumference of the inner surface 220. Other configurations are also contemplated herein.

Figure 5:
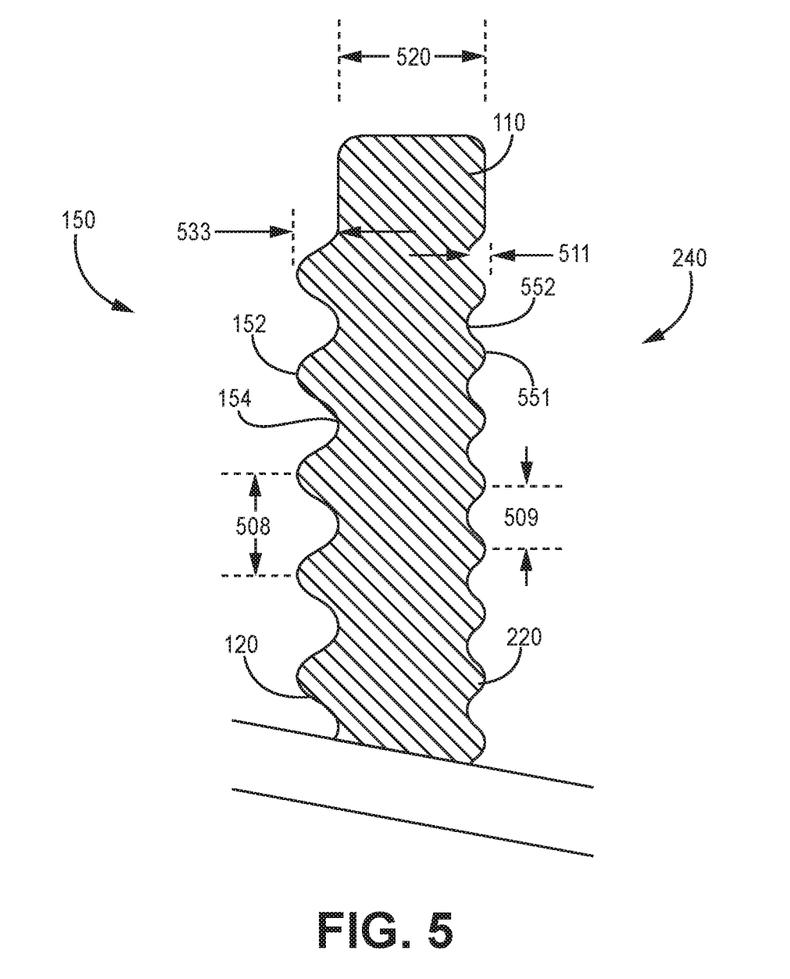
FIG. 5 is a cross-sectional view of the polymeric wall member of the socket liner of FIG. 1.

FIG. 5 is a cross-sectional view of the polymeric wall member 110 of the socket liner 100 as taken along the line 5-5' of FIG. 4. The view of FIG. 5 shows the outer surface 120 having a plurality of exterior horizontal ridges 150 with a plurality of peaks 152 and a plurality of troughs 154. In the example of FIG. 5, the peaks 152 and the troughs 154 create a sinusoidal pattern with curved peaks 152 and curved troughs 154; however, other cross-sectional shapes for the peaks and troughs are possible. For example, the peaks 152 can be semicircular, and the troughs 154 can be planar or V-shaped. Other cross-sectional shapes are contemplated herein, including but not limited to polygonal shapes, such as square or rectangular shapes, or the like.

In some examples, the peak-to-trough height 533 of the plurality of exterior horizontal ridges 150 is about 0.05, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.5 or 4.0 mm or in a range between any of the foregoing heights so long as the upper bound is greater than the lower bound. In alternative examples, the peak-to-trough height 533 can be between 1.2 and 1.6 mm. Other dimensions are also contemplated herein.

The plurality of exterior horizontal ridges 150 can have a pitch 508, which is defined as the distance between a first peak and a second, adjacent peak along the length of the outer surface 120. In some examples, the pitch 508 can be approximately 2, 4, 6, 8, 10, 12, 14, 16, 18, 20, 22, 24 or 26 mm. In some embodiments, the pitch 508 can fall within a range wherein any of the foregoing can serve as the upper or lower bound of the range, provided that the upper bound is greater than the lower bound. In some embodiments, the pitch 508 can be between approximately 10 mm and 18 mm. In some examples, the pitch 508 is uniform along the length of the outer surface 120; that is, the distance between adjacent peaks is the same near the open upper end 130 as it is near the closed lower end 140. In alternative examples, the pitch 508 is variable along the length of the outer surface 120. As such, in some embodiments herein the pitch measurements can refer to an average. In some examples, the pitch for a first peak and a second, adjacent peak at the anterior side 121 of the polymeric wall member 110 is larger than the pitch for the first peak and the second peak at the posterior side 122 of the polymeric wall member 110.

FIG. 5 also shows the plurality of horizontal ridges 240 on the inner surface 220 of the polymeric wall member 110. The horizontal ridges 240 have peaks 551 and troughs 552. In the example of FIG. 5, the peaks 551 and the troughs 552 create a sinusoidal pattern with curved peaks 551 and curved troughs 552; however, other cross-sectional shapes for the peaks and troughs are possible. For example, the peaks 551 can be semicircular, and the troughs 552 can be planar or V-shaped. Other cross-sectional shapes are contemplated herein, including but not limited to polygonal shapes, such as square or rectangular shapes, or the like. The horizontal ridges 240 increase the coefficient of friction between the polymeric wall member 110 and the user's skin.

Additionally, the orientation of the horizontal ridges 240 is approximately perpendicular to the longitudinal direction of a user's residual limb. In some cases, conventional socket liners are most likely to slip in a vertical direction, that is, along the lengthwise axes 101, 102 of the socket liner 100 as shown in FIG. 1. The horizontal ridges 240 shown in FIGS. 2 and 5, extending perpendicular to the lengthwise axes 101, 102, generate crosswise friction against the user's skin that opposes movement or slipping of the socket liner 100 down the direction of the lengthwise axes.

In some examples, the peak-to-trough height 511 of the plurality of horizontal ridges 240 is between 0.05 mm and 2 mm. In some examples, the peak-to-trough height 511 is about 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0 mm, or in a range between any of the foregoing heights so long as the upper bound is greater than the lower bound. Other dimensions are possible, depending on the individual requirements for a user.

The plurality of horizontal ridges 240 can have a pitch 509, which is defined as the distance between a first peak and a second, adjacent peak along the length of the inner surface 220. In various embodiments, the pitch 509 of the horizontal ridges 240 on the inner surface 220 can be less than the pitch 508 of the exterior horizontal ridges 150. In some examples, the pitch 509 can be about 1.0, 1.5, 2.0, 2.5, 3.0, 3.5, 4.0, 4.5, 5.0, 5.5, or 6.0 mm. In some examples, the pitch 509 can fall within a range wherein any of the foregoing can serve as the upper or lower bound of the range, provided that the upper bound is greater than the lower bound.

In some examples, the pitch 509 is uniform along the length of the inner surface 220; that is, the distance between adjacent peaks is the same near the open upper end 130 as it is near the closed lower end 140. In alternative examples, the pitch 509 is variable along the length of the inner surface 220. In some examples, the pitch 509 is uniform along the circumference of the inner surface 220. In alternative examples, the pitch 509 can be non-uniform.

In some embodiments, the width 520 of the polymeric wall member 110 can have a substantially constant thickness along the length from the upper portion 131 to the lower portion 141 of the socket liner 100. In other embodiments, the width 520 of the polymeric wall member 110 can have a variable thickness along the length from the upper portion 131 to the lower portion 141 of the socket liner 100. The average thickness of the polymeric wall member 110 can be averaged along the length of the cross-section shown in FIG. 5.

The width 520 of the polymeric wall member 110 can vary. In some examples, the width is about 1.0, 1.5, 2.0, 2.5, 3.0, 3.5, 4.0, 4.5, 5.0, 5.5, 6.0, 7.0, 7.5, 8.0 or 10.0 mm. In some embodiments, the width of the polymeric wall can fall within a range wherein any of the foregoing widths can serve as the upper or lower bound of the range, provided that the upper bound is greater than the lower bound.

The exterior horizontal ridges 150 can have a different peak-to-trough height 533 than the peak-to-trough height 511 of the horizontal ridges 240. In some examples, the exterior height 533 is greater than the interior height 511. In some examples, the pitch 508 of the exterior horizontal ridges 150 is different from the pitch 509 of the horizontal ridges 240. In some examples, the exterior pitch 508 is larger than the interior pitch 509.

Figure 6:
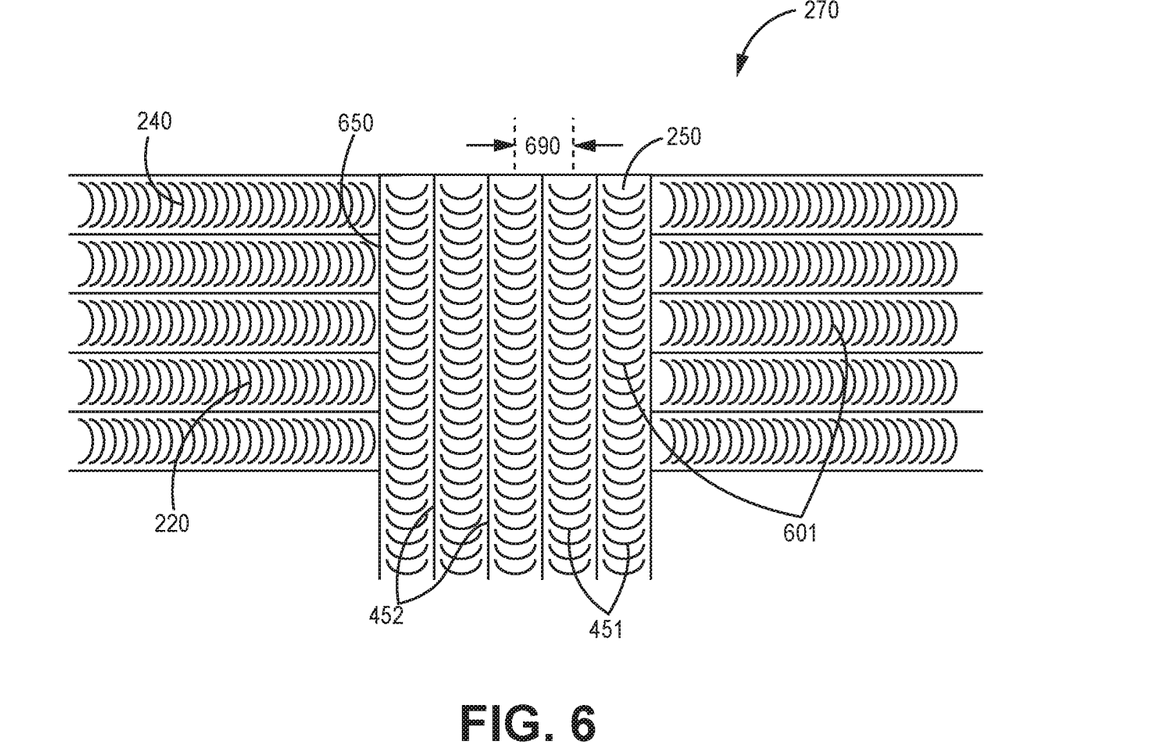
FIG. 6 is a close-up view of an inner surface for a socket liner for a prosthetic in accordance with various embodiments herein.

Turning to FIG. 6, a close-up view of an inner surface for a socket liner is shown. The drawing of FIG. 6 shows the socket liner 100 as though it were a flat plane, but in use, the subject matter of FIG. 6 would be curved. The inner surface 220 includes a plurality of vertical channels 250 on an anterior side 121 of the polymeric wall member 110 and a plurality of horizontal ridges 240 on a first lateral side 270 and a second lateral side 480. In some embodiments, the vertical channels 250 on the anterior side 121 can intersect the horizontal ridges 240 on the second lateral side 480 at an intersection boundary 650.

In the example of FIG. 6, the vertical channels 250 and the horizontal ridges 240 can include microribbing 601. The microribbing 601 is a surface texture on the inner surface 220 that serves to increase the coefficient of friction between the inner surface 220 and the user's skin. In some examples, the microribbing 601 consists of many minute peaks and troughs that further increase the surface area of the inner surface 220. The microribbing 601 can be a plurality of parallel curved peaks and troughs. In alternative examples, the microribbing 601 can be a plurality of bumps or other structural features that increases the surface area of the inner surface 220. The microribbing 601 can be present on both the vertical channels 250 and the horizontal ridges 240. The microribbing 601 can be substantially perpendicular to the lengthwise axis of the vertical channels 250 and/or horizontal ridges 240 they are disposed on. It will be appreciated, however, that various embodiments do not include microribbing.

FIG. 6 also shows the plurality of peaks 451 and the plurality of troughs 452 of the vertical channels 250. The vertical channels have a pitch 690 that is defined as the distance between a first peak 451 and a second, adjacent peak 451. In some examples, the pitch of the vertical channels 250 is approximately 1.0, 1.5, 2.0, 2.5, 3.0, 3.5, 4.0, 4.5, 5.0, 5.5, 6.0, 7.0, 7.5, or 8.0 mm. In some embodiments, the pitch of the vertical channels 250 can fall within a range wherein any of the foregoing can serve as the upper or lower bound of the range, provided that the upper bound is greater than the lower bound. Other configurations are also contemplated herein. For example, the complementary sinusoidal pattern shown in FIG. 3 of the plurality of peaks 351 and the plurality of troughs 352 could be combined with the microribbing 601 of FIG. 6.

Figure 7:
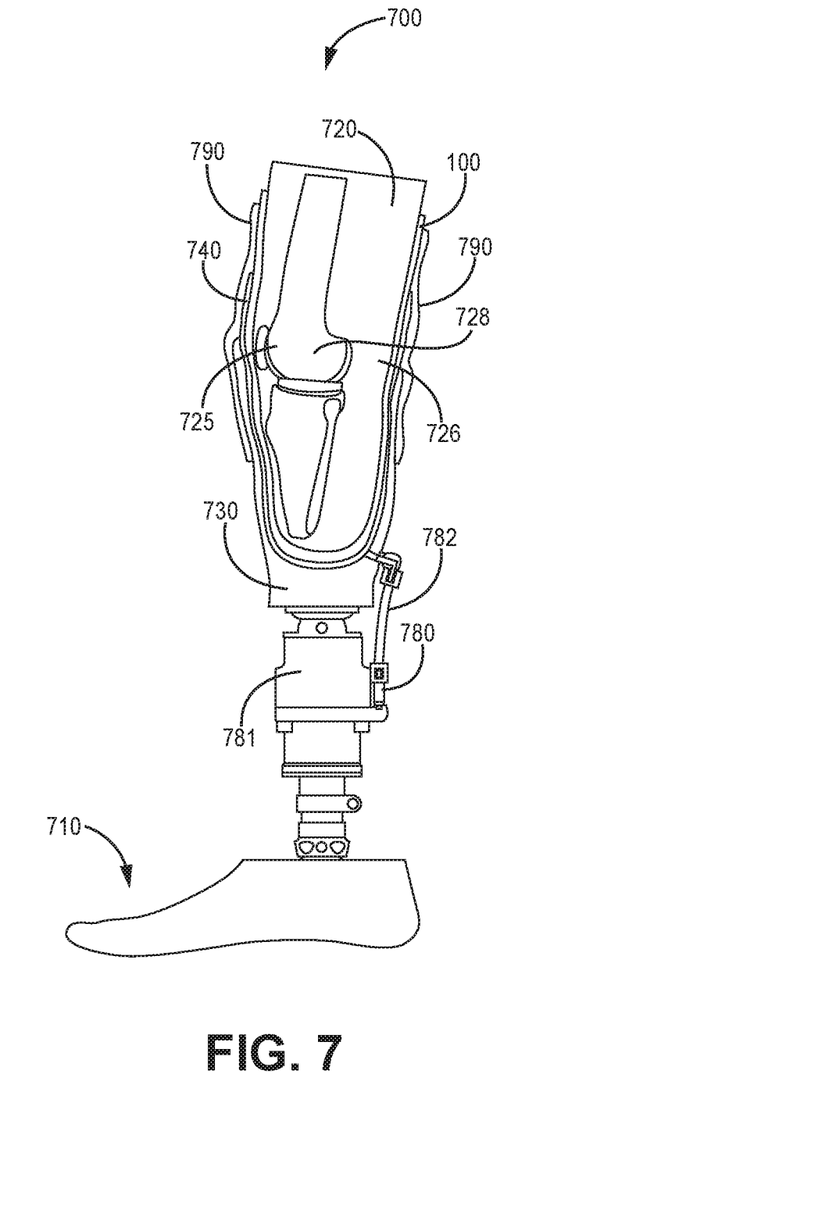
FIG. 7 is a cross-sectional view of a prosthetic system in accordance with various embodiments herein.

FIG. 7 is a cross-sectional view of a prosthetic system 700 using the socket liner 100 shown and described with respect to FIGS. 1-6. In some embodiments, the system 700 can be a total surface bearing (TSB) system with a combined suction and vacuum suspension. Aspects of TSB systems as described in U.S. Pat. No. 8,114,167, the content of which is hereby incorporated by reference in its entirety. However, the socket liner 100 could also be incorporated into other types of prosthetic systems. One of ordinary skill in the art will appreciate that the use of the socket liner 100 is not limited to the particular prosthetic system described herein.

The system 700 can include a socket 730 configured to receive a residual limb 720. The socket liner 100 includes a polymeric wall member 110 defining interior volume 115. Some aspects of the size and shape of the socket liner 100 and the prosthetic foot 710 can be determined individually for each user. The user's residual limb 720 includes a knee joint 728 which has an anterior portion 725 and a posterior portion 726. In some examples, the anterior side 121 of the socket liner 100 is aligned with the anterior portion 725 of the knee joint, and the posterior side 122 of the socket liner 100 is aligned with the posterior portion 726 of the knee joint. The vertical channels 250 on the inner surface 220 thus are aligned with the anterior portion 725 and the posterior portion 726 of the knee joint 728.

The socket liner 100 is disposed over the residual limb 720 in FIG. 7, and the residual limb 720 and the socket liner 100 are disposed inside of the total surface bearing socket 730. A number of factors work together to secure the socket liner 100 to the user's skin. The inner surface 220 of the socket liner 100 is configured to releasably adhere to a user's skin while the socket liner 100 is worn over a residual limb. In some examples, the socket liner 100 is sized such that almost no air is present between the inner surface 220 of the socket liner 100 and the user's skin.

In some examples, a sock 740 is disposed between the socket liner 100 and the socket 730, however, this is not essential. A sealing sleeve 790 encloses the outer surface 120 of socket liner 100 and the outer surface of the socket 730. This allows a vacuum pump 781 to remove air from the space between the exterior surface of the socket liner 100 and the interior surface of the socket 730 through a hose 782 via a one-way valve 780.

While FIG. 7 shows a transtibial (below knee) prosthesis, it will be appreciated that aspects of embodiments herein can also be used with socket liners for other types of prostheses including those of the lower and upper extremities. By way of examples, aspects of liners described herein can also be used in conjunction with prostheses for partial foot amputations, through the ankle amputations, knee disarticulation amputations, above the knee amputations, hip disarticulation amputations, hemi-pelvectomies, wrist disarticulations, below the elbow amputations, elbow disarticulation amputations, above the elbow amputations, shoulder disarticulations, and the like.

A method of making a socket liner is also included herein. The method includes taking a cast of a residual limb of an amputee. In some examples, multiple casts are taken of the residual limb. For example, three casts can be taken, with the limb in a different degree of flexion or extension in each cast. The multiple casts are used to mold a single socket liner having at least some of the qualities shown and described in relation to FIGS. 1 through 7. In some embodiments, the socket liner can be pre-flexed such that when not in use, the socket liner exhibits a first lengthwise axis and a second lengthwise axis that intersect at the location of a joint.

In some examples, the cast is used to form a mold. The mold can comprise a female mold for shaping an outer surface of the socket liner, and a male mold for shaping the inner surface of the socket liner.

Figure 8:
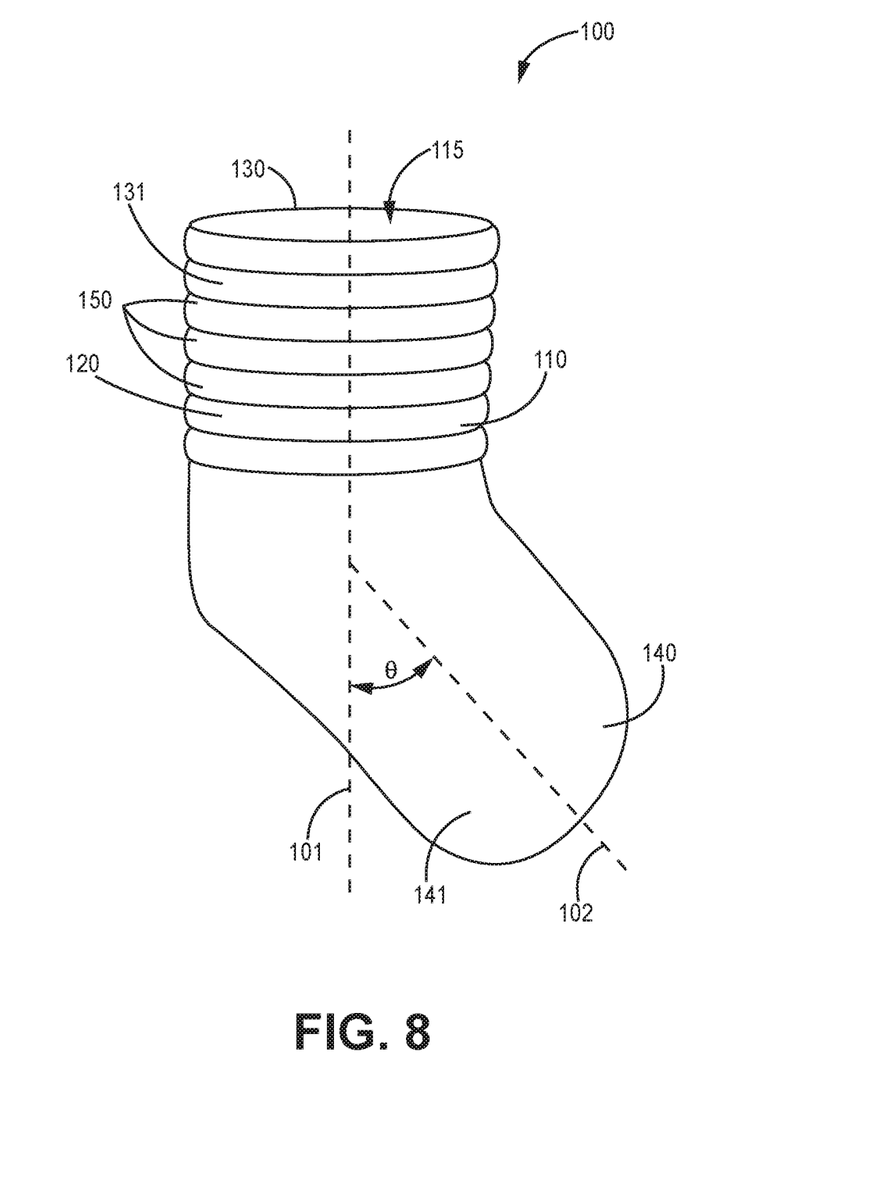
FIG. 8 is a side view of a socket liner for a prosthetic in accordance with various embodiments herein.

Referring now to FIG. 8, a side view is shown of a socket liner 100 for a prosthetic in accordance with various embodiments herein. FIG. 8 is generally similar to FIG. 1, except for the placement of exterior horizontal ridges 150 thereon. The socket liner 100 includes a polymeric wall member 110 defining an interior volume 115. The socket liner 100 is shaped to cover a residual limb for an amputee. The socket liner 100, as defined by the polymeric wall member 110, has an open upper end 130 at an upper portion 131 of the polymeric wall member 110, and a closed lower end 140 at a lower portion 141 of the polymeric wall member 110.

In the example of FIG. 8, the socket liner 100 has an anterior side 121 that aligns with an anterior portion of a knee joint. Opposite the anterior side 121 is a posterior side 122 of the socket liner 100. The posterior side 122 aligns with a posterior portion of the knee joint. In some examples, the socket liner 100 is pre-flexed, that is, shaped to conform to the geometry of a limb in partial flexion, with the knee slightly bent instead of having the knee fully extended. In such a case, the socket liner 100 includes a first lengthwise axis 101 that generally aligns with the user's femur, and a second lengthwise axis 102 that generally aligns with the user's lower leg. The first lengthwise axis 101 and the second lengthwise axis 102 are configured to intersect at or about the user's knee joint. In some examples, the angle between the first lengthwise axis 101 and the second lengthwise axis 102 is between 0 degrees and 45 degrees or between 10 degrees and 45 degrees.

An outer surface 120 of the polymeric wall member 110 can have a plurality of exterior horizontal ridges 150. In some examples, the exterior horizontal ridges 150 extend 360 degrees around the outer circumference of the socket liner 100. In some examples, the exterior horizontal ridges 150 can extend for less than 360 degrees around the outer circumference. In some examples, the exterior horizontal ridges 150 extend up to the open upper end 130, but in other embodiments do not extend that high. In the example of FIG. 8, the exterior horizontal ridges 150 begin at the top of open upper end 130 but end above where flexion must occur during use of the socket liner (in contrast to FIG. 1). In some embodiments, the exterior horizontal ridges 150 end above the wearer's meniscus. In some embodiments, the exterior horizontal ridges 150 end above the wearer's femoral condyles. In some embodiments the exterior horizontal ridges 150 end approximately 0.5, 1, 2, 3, 4, 5, 6, 7, 8, 9, 10, 11, or 12 centimeters above the user's meniscus.

Figure 9:
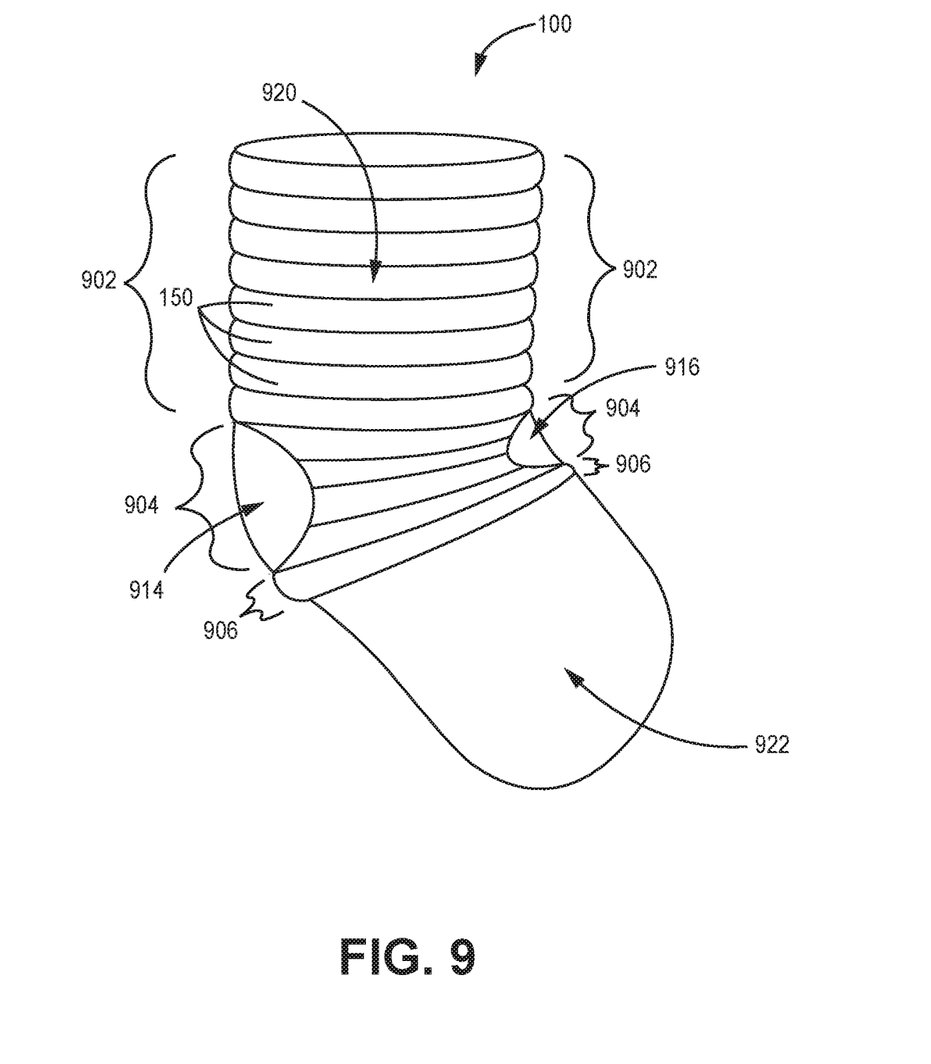
FIG. 9 is a side view of a socket liner for a prosthetic in accordance with various embodiments herein.

In some embodiments, ridges can have a different morphology in the area of the user's knee in order to facilitate easier flexion. As one example, ridges can be made thinner or even removed in the area of the user's knee at posterior and/or anterior positions. Referring now to FIG. 9, a side view is shown of a socket liner 100 for a prosthetic in accordance with various embodiments herein. FIG. 9 is generally similar to FIG. 1, except for the morphology of some of the exterior horizontal ridges 150 thereon. In particular, the socket liner 100 can include a proximal portion 920 including exterior horizontal ridges 150 and distal portion 922 lacking exterior horizontal ridges 150. The proximal portion 920 can include a first contoured segment 902, a second contoured segment, 904, and a third contoured segment 906. In various embodiments, the first contoured segment 902 can correspond to an area generally above the knee, the second contoured segment 904 can correspond to an area representing the knee, and the third contoured segment 906 can correspond to an area below the knee. In this view, the anterior side of the second contoured segment 904 can include an area 914 with a different ridge morphology. In area 914, the exterior horizontal ridges can be substantially reduced in size and in some embodiments can be non-existent. Also, in this view, the posterior side of the second contoured segment 904 can include an area 916 with a different ridge morphology. In area 916, the exterior horizontal ridges can be substantially reduced in size and in some embodiments can be non-existent. While not intending to be bound by theory, altering the morphology of the ridges in areas 914, 916 is believed to aid in allowing bending of the knee to occur while also preventing bunching or misarrangement of the socket liner 100. In some embodiments, the size/width/thickness/etc. of the exterior horizontal ridges 150 in areas 914, 916 can be reduced by 20, 30, 40, 50, 60, 70, 80, 90 or 100 percent. In some embodiments, the boundaries of areas 914 and/or 916 are largest (e.g., the boundary extends farthest toward the lateral side) at or near their midpoint with respect to a proximal to distal axis of the socket liner 100. In some embodiments, the boundary of areas 914 and/or 916 forms a curvilinear shape. In some embodiments, the boundary of areas 914 and/or 916 forms a semicircular shape extending inward toward the lateral side.

Polymers

The polymeric wall member can be made of various different types of polymer. In some embodiments, the polymeric wall member can be formed of a thermoplastic polymer. In some embodiments, the polymeric wall member can be formed of a thermoplastic elastomeric polymer. In some embodiments, the polymeric wall member can be formed of a thermoset polymer. In some embodiments, the polymeric wall member can be formed of a single polymer. In other embodiments, the polymeric wall member can be formed from two or more polymers forming a mixture or alloy. In some embodiments, the polymeric wall member can be formed of a homopolymer. In other embodiments, the polymeric wall member can be formed of a copolymer or terpolymer.

In some embodiments, the polymeric wall member can be made of a silicone, urethane, and thermoplastic elastomers (TPE) gels. In some embodiments, the polymeric wall member can be formed of a composition including one or more block copolymers and mineral oil. In some embodiments, the polymeric wall member can also include one or more antioxidants, skin conditioning agents, astringents, biocides, medicaments, etc. In some embodiments, the polymeric wall member can include a tackifier. In some embodiments, the polymeric wall member can exhibit a tacky surface property. In some embodiments, the polymeric wall member can include a surface coating to increase the tackiness of the surface.

In some embodiments, the polymeric wall member can be made of a polyurethane polymer. In some embodiments, the polyurethane polymer can be uncrosslinked. However, in other embodiments, the polyurethane polymer can be crosslinked. In some embodiments, the polyurethane is a thermoplastic polyurethane elastomer. The polyurethane can be a block copolymer consisting of alternating sequences of hard and soft segments or domains. Polyurethanes can be formed by reacting an isocyanate containing two or more isocyanate groups per molecule with a polyol containing on average two or more hydroxyl groups per molecule. Various isocyanates can be used, including, but not limited to aromatic diisocyanates such as toluene diisocyanate and methylene diphenyl diisocyanate. In various embodiments, polyurethanes can be formed by reacting an isocyanate compound with a prepolymer, wherein aspects of the resulting polyurethane can be controlled by manipulating the amount of isocyanate compound used relative to the amount of the prepolymer. The prepolymer can be of various molecular weights such, as 1000, 2000, 3000, 4000, 5000, 6000, 7000, 8000, 10,000, or more, or falling within a range between any of the foregoing. In some embodiments, the polyurethane can be polyether-based. However, in other embodiments the polyurethane can be polyester-based. Aspects of polyurethane elastomers are described in U.S. Pat. Nos. 5,081,210; 7,019,082; 9,556,305; the content of which related to elastomeric polymers is herein incorporated by reference.

In various embodiments, the polymeric material provides a specific firmness, yet has the proper rebound characteristics for shock absorption and energy transfer. In some examples, the polymeric wall member can be made of a polymer having a durometer value of 50 to 80 on a 00 scale. In some embodiments, the durometer value can be about 50, 55, 60, 65, 70, 75, or 80 on a 00 scale. In some embodiments, the durometer value can fall in a range between any of the foregoing durometer values. In some embodiments, the durometer value can be from 55 to 75, from 55 to 70, or from 65 to 70 on a 00 scale. Durometer values can be measured in accordance with ASTM D2240.

It should be noted that, as used in this specification and the appended claims, the singular forms "a," "an," and "the" include plural referents unless the context clearly dictates otherwise. Thus, for example, reference to a composition containing "a compound" includes a mixture of two or more compounds. It should also be noted that the term "or" is generally employed in its sense including "and/or" unless the context clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this specification pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications can be made while remaining within the spirit and scope herein. As such, the embodiments described herein are not intended to be exhaustive or to limit the scope to the precise forms disclosed herein. Rather, the embodiments are chosen and described so that others skilled in the art can appreciate and understand the principles and practices.

The invention claimed is:

1. A socket liner for a prosthetic system, the socket liner comprising:
    a polymeric wall member defining an interior volume, the polymeric wall member having an inner surface bordering the interior volume and an outer surface on the opposite side of the polymeric wall member from the inner surface;
    the polymeric wall member comprising
        an anterior side,
        a posterior side,
        a first lateral side, and
        a second lateral side, the second lateral side opposite the first lateral side
    the polymeric wall member comprising an open upper end and a closed lower end;
    a plurality of horizontal ridges disposed on the inner surface of the polymeric wall member on the first lateral side and the second lateral side; and
    a plurality of vertical channels disposed on the inner surface of the polymeric wall member on the anterior side and the posterior side, the plurality of vertical channels forming a transport conduit up to the open upper end for moisture to move out of the socket liner;
    wherein at least some of the plurality of horizontal ridges intersect at least some of the vertical channels;
    wherein the plurality of horizontal ridges terminate where they intersect with the plurality of vertical channels.

2. The socket liner of claim 1, further comprising a plurality of exterior horizontal ridges disposed on the outer surface of the polymeric wall member.

3. The socket liner of claim 2, the exterior horizontal ridges having a pitch that is different than a pitch of the horizontal ridges disposed on the inner surface of the polymeric wall member.

4. The socket liner of claim 2, the exterior horizontal ridges having a pitch of 10 mm to 18 mm.

5. The socket liner of claim 2, the exterior horizontal ridges having a peak to trough height of 0.1 to 4.0 mm.

6. The socket liner of claim 1, the horizontal ridges disposed on the inner surface of the polymeric wall member having a pitch of 1.0 to 6.0 mm.

7. The socket liner of claim 1, the horizontal ridges disposed on the inner surface of the polymeric wall member having a peak to trough height of 0.05 mm to 2 mm.

8. The socket liner of claim 1, the vertical channels having a pitch of about 1 to 8 mm.

9. The socket liner of claim 1, the vertical channels having a peak to trough height of 0.05 mm to 2 mm.

10. The socket liner of claim 1, wherein the inner surface of the polymeric wall member has a surface area that is at least about 50 percent greater than an otherwise identical polymeric wall member lacking the plurality of horizontal ridges disposed on the inner surface and the plurality of vertical channels.

11. The socket liner of claim 1, the polymeric wall member comprising a thermoplastic polymer.

12. The socket liner of claim 1, the polymeric wall member comprising a polyurethane polymer.

13. The socket liner of claim 1, the polymeric wall member comprising a polymer having a durometer value of 50 to 80 on a 00 scale.

14. The socket liner of claim 1, the polymeric wall member having an average thickness between the inner surface and the outer surface of 2 mm to 10 mm.

15. The socket liner of claim 1, the closed lower end comprising a substantially hemispherical shape.

16. The socket liner of claim 1, the polymeric wall member comprising an upper portion with a first lengthwise axis and a lower portion with a second lengthwise axis wherein the first lengthwise axis and the second lengthwise axis intersect at an angle of between 10 degrees and 45 degrees.

17. A socket liner interface system comprising:
a prosthesis comprising a socket configured to receive a residual limb; and
a socket liner comprising a polymeric wall member defining an interior volume, the polymeric wall member having an inner surface bordering the interior volume and an outer surface on the opposite side of the polymeric wall member from the inner surface;
the polymeric wall member comprising
an anterior side,
a posterior side,
a first lateral side, and
a second lateral side, the second lateral side opposite the first lateral side;
the polymeric wall member comprising an open upper end and a closed lower end;
a plurality of horizontal ridges disposed on the inner surface of the polymeric wall member on the first lateral side and the second lateral side; and
a plurality of vertical channels disposed on the inner surface of the polymeric wall member on the anterior side and the posterior side, the plurality of vertical channels forming a transport conduit up to the open upper end for moisture to move out of the socket liner;
the plurality of horizontal ridges terminating where they intersect with the plurality of vertical channels.

18. The socket liner interface system of claim 17, further comprising a plurality of exterior horizontal ridges disposed on the outer surface of the polymeric wall member.

19. A socket liner for a prosthetic system, the socket liner comprising:
a polymeric wall member defining an interior volume, the polymeric wall member having an inner surface bordering the interior volume and an outer surface on the opposite side of the polymeric wall member from the inner surface;
the polymeric wall member comprising
an anterior side,
a posterior side,
a first lateral side, and
a second lateral side, the second lateral side opposite the first lateral side
the polymeric wall member comprising an open upper end and a closed lower end;
a plurality of horizontal ridges disposed on the inner surface of the polymeric wall member on the first lateral side and the second lateral side; and
a plurality of vertical channels disposed on the inner surface of the polymeric wall member on the anterior side and the posterior side, the plurality of vertical channels forming a transport conduit up to the open upper end for moisture to move out of the socket liner;
wherein the plurality of horizontal ridges do not overlap the plurality of vertical channels.

* * * * *